(12) United States Patent
Lee et al.

(10) Patent No.: US 8,039,635 B2
(45) Date of Patent: Oct. 18, 2011

(54) N-HYDROXY-4-{5-[4-(5-ISOPROPYL-2-METHYL-1,3-THIAZOL-4-YL) PHENOXY]PENTOXY} BENZAMIDINE 2 ETHANSULFONIC ACID SALT, PROCESS FOR THE PREPARATION THEREOF AND PHARMACEUTICAL COMPOSITION COMPRISING THE SAME

(75) Inventors: Jin Soo Lee, Gyeonggi-do (KR); Soon Ki Cho, Gyeonggi-do (KR); Seoung Kyoo Sung, Gyeonggi-do (KR); Young Goo Jin, Gyeonggi-do (KR); Jae Hoon Park, Seoul (KR); Bo Kyung Kim, Gyeonggi-do (KR); Ja Hyun Cha, Incheon (KR); Eun Hee Cho, Gyeonggi-do (KR); Jei Man Ryu, Gyeonggi-do (KR)

(73) Assignee: Dong Wha Pharmaceutical Co., Ltd., Seoul (KR)

( * ) Notice: Subject to any disclaimer, the term of this patent is extended or adjusted under 35 U.S.C. 154(b) by 184 days.

(21) Appl. No.: 12/531,807

(22) PCT Filed: Apr. 21, 2008

(86) PCT No.: PCT/KR2008/002246
§ 371 (c)(1),
(2), (4) Date: Sep. 17, 2009

(87) PCT Pub. No.: WO2008/130172
PCT Pub. Date: Oct. 30, 2008

(65) Prior Publication Data
US 2010/0113538 A1    May 6, 2010

(30) Foreign Application Priority Data
Apr. 19, 2007   (KR) .................. 10-2007-0038395

(51) Int. Cl.
*A61K 31/426*   (2006.01)
*C07D 277/30*   (2006.01)
(52) U.S. Cl. .............................. 548/202; 514/365
(58) Field of Classification Search ............... 548/202
See application file for complete search history.

(56) References Cited

FOREIGN PATENT DOCUMENTS

| WO | WO 03-007947 A1 | 1/2003 |
|---|---|---|
| WO | WO 2006-004369 A1 | 1/2006 |
| WO | WO 2006-004370 A1 | 1/2006 |
| WO | WO 2006-057501 A1 | 6/2006 |
| WO | WO 2006-057507 A1 | 6/2006 |

*Primary Examiner* — Laura L. Stockton
(74) *Attorney, Agent, or Firm* — Arent Fox LLP

(57) ABSTRACT

N-hydroxy-4-{5-[4-(5-isopropyl-2-methyl-1,3-thiazol-4-yl) phenoxy]pentoxy} benzamidine 2 ethansulfonic acid salt, a process for the preparation thereof, a pharmaceutical composition for preventing and treating osteoporosis, bone fractures or allergic inflammatory diseases, comprising the same, and an oral formulation for preventing and treating osteoporosis, bone fractures or allergic inflammatory diseases, comprising the same are described.

10 Claims, No Drawings

N-HYDROXY-4-{5-[4-(5-ISOPROPYL-2-METHYL-1,3-THIAZOL-4-YL) PHENOXY]PENTOXY} BENZAMIDINE 2 ETHANSULFONIC ACID SALT, PROCESS FOR THE PREPARATION THEREOF AND PHARMACEUTICAL COMPOSITION COMPRISING THE SAME

CROSS-REFERENCE TO RELATED APPLICATION

This application is a 371 National Stage entry of International Application No. PCT/KR2008/002246 filed Apr. 21, 2008, now WO 2008/130172 with an International Publication date of Oct. 30, 2008, which claims the benefit of priority to KR 10-2007-0038395, filed Apr. 19, 2007, the entire specification, claims and drawings of which are incorporated herewith by reference.

TECHNICAL FIELD

The present invention relates to an N-hydroxy-4-{5-[4-(5-isopropyl-2-methyl-1,3-thiazol-4-yl)phenoxy]pentoxy}benzamidine 2 ethansulfonic acid salt, a process for the preparation thereof, a pharmaceutical composition for preventing and treating osteoporosis, bone fractures or allergic inflammatory diseases, comprising the same, and an oral formulation for preventing and treating osteoporosis, bone fractures or allergic inflammatory diseases, comprising the same.

BACKGROUND ART

N-hydroxy-4-{5-[4-(5-isopropyl-2-methyl-1,3-thiazol-4-yl)phenoxy]pentoxy}benzamidine has excellent efficacy in the treatment and prevention of osteoporosis (Korean Patent No. 10-454767), in the treatment of bone fractures (Korean Patent No. 10-639041), and in the treatment and prevention of allergic inflammatory diseases (Korean Patent No. 10-682199).

It is generally known to those skilled in the art that active ingredients used in pharmaceutical compositions must be highly soluble in water or an aqueous solution of a broad range of pH values. However, since N-hydroxy-4-{5-[4-(5-isopropyl-2-methyl-1,3-thiazol-4-yl)phenoxy]pentoxy}benzamidine has low solubility, its salt forms having high solubility need to be developed to increase bioavailability of the compound.

Accordingly, the present inventors have developed an N-hydroxy-4-{5-[4-(5-isopropyl-2-methyl-1,3-thiazol-4-yl)phenoxy]pentoxy}benzamidine 2 methansulfonic acid salt, which is highly soluble and stable (Korean Patent Publication No. 10-2006-57511).

DISCLOSURE OF INVENTION

Technical Problem

Accordingly, the present inventors have conducted studies to develop a salt form having better physicochemical properties such as stability, solubility, and bioavailability than the previously invented N-hydroxy-4-{5-[4-(5-isopropopyl-2-methyl-1,3-thiazol-4-yl)phenoxy]pentoxy}benzamidine 2 methansulfonic acid salt. Thus, the present inventors synthesized an N-hydroxy-4-{5-[4-(5-isopropyl-2-methyl-1,3-thiazol-4-yl)phenoxy]pentoxy}benzamidine 2 ethansulfonic acid salt, and they found that the 2 ethansulfonic acid salt thereof has excellent solubility, stability, and bioavailability, as well as a higher initial release rate, than 2 methansulfonic acid salt thereof, thereby completing the present invention.

Technical Solution

It is an object of the present invention to provide an N-hydroxy-4-{5-[4-(5-isopropyl-2-methyl-1,3-thiazol-4-yl)phenoxy]pentoxy}benzamidine 2 ethansulfonic acid salt, a process for the preparation thereof, a pharmaceutical composition for preventing and treating osteoporosis, bone fractures or allergic inflammatory diseases, comprising the same, and an oral formulation for preventing and treating osteoporosis, bone fractures or allergic inflammatory diseases, comprising the same.

BEST MODE FOR CARRYING OUT THE INVENTION

In one aspect, the present invention relates to an N-hydroxy-4-{5-[4-(5-isopropyl-2-methyl-1,3-thiazol-4-yl)phenoxy]pentoxy}benzamidine 2 ethansulfonic acid salt, represented by the following Formula 1.

<Formula 1>

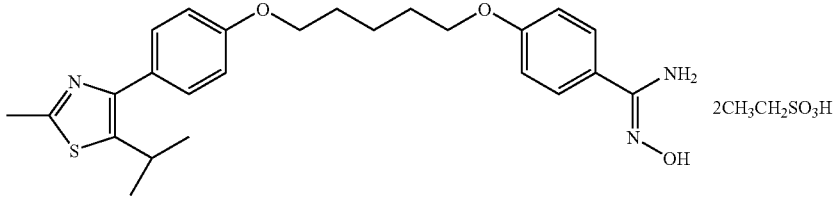

$2CH_3CH_2SO_3H$

N-hydroxy-4-{5-[4-(5-isopropyl-2-methyl-1,3-thiazol-4-yl)phenoxy]pentoxy}benzamidine is disclosed in the literature (Lee, Sung-Eun, Synthesis and Biological Activity of Natural Products and Designed New Hybrid Compounds for the Treatment of LTB4 Related Disease, Busan National University, a thesis for a Ph. D degree, August 1999).

As used herein, the term "2 ethansulfonic acid salt" refers to a compound in which two ethanesulfonic acid molecules are bonded to one free base compound to form a salt, and with respect to the present objects, indicates a 2 ethanesulfonic acid salt of N-hydroxy-4-{5-[4-(5-isopropyl-2-methyl-1,3-thiazol-4-yl)phenoxy]pentoxy}benzamidine.

The present inventors found that a 2 ethanesulfonic acid salt, in which two ethanesulfonic acid molecules are bonded to the N-hydroxy-4-{5-[4-(5-isopropyl-2-methyl-1,3-thiazol-4-yl)phenoxy]pentoxy}benzamidine compound having low solubility, has higher solubility, initial release rate, and stability, and exerts remarkably higher bioavailability in vivo, than a 2 methanesulfonic acid salt in which two methanesulfonic acid molecules is bonded to the benzamidine compound.

In detail, the 2 ethanesulfonic acid salt of N-hydroxy-4-{5-[4-(5-isopropyl-2-methyl-1,3-thiazol-4-yl)phenoxy]pentoxy}benzamidine according to the present invention exhibited solubility about 1.25-fold higher in distilled water and release rate about 2.8-fold higher after 5 min, about 1.4-fold higher after 10 min, and about 1.2-fold higher after 15 min, as compared to the 2 methanesulfonic acid salt thereof. Also, in a stability test under severe conditions of 60° C. for 2 weeks, there is no change in its content, and it exhibits excellent chemical stability at high temperature. Moreover, when administered to the body, the 2 ethanesulfonic acid salt displayed high bioavailability of 1.3-fold higher Cmax (maximum blood concentration), 1.4-fold faster Tmax (time to reach maximum plasma concentration), and about 1.2-fold higher AUC (area under the blood concentration-time curve), as compared to the 2 methanesulfonic acid salt of the benzamidine compound.

The 2 ethanesulfonic acid salt of N-hydroxy-4-{5-[4-(5-isopropyl-2-methyl-1,3-thiazol-4-yl)phenoxy]pentoxy}benzamidine according to the present invention may be in a crystal or non-crystal form. Preferred is a crystal form of the 2 ethanesulfonic acid salt of N-hydroxy-4-{5-[4-(5-isopropyl-2-methyl-1,3-thiazol-4-yl)phenoxy]pentoxy}benzamidine.

In another aspect, the present invention relates to a process for preparing the 2 ethanesulfonic acid salt of N-hydroxy-4-{5-[4-(5-isopropyl-2-methyl-1,3-thiazol-4-yl)phenoxy]pentoxy}benzamidine of Formula 1.

In detail, the present invention provides a process for preparing the 2 ethanesulfonic acid salt of N-hydroxy-4-{5-[4-(5-isopropyl-2-methyl-1,3-thiazol-4-yl)phenoxy]pentoxy}benzamidine, comprising the step of reacting N-hydroxy-4-{5-[4-(5-isopropyl-2-methyl-1,3-thiazol-4-yl)phenoxy]pentoxy}benzamidine and ethanesulfonic acid in an inert solvent, which is represented by the following Reaction Scheme 1.

In the inert solvent, one equivalent of N-hydroxy-4-{5-[4-(5-isopropyl-2-methyl-1,3-thiazol-4-yl)phenoxy]pentoxy}benzamidine is reacted with 2 to 4 equivalents, preferably 2.1 to 2.5 equivalents, of ethanesulfonic acid, at −20° C. to 40° C., preferably 0° C. to 20° C., for 10 min to 5 hrs, preferably 30 min to 2 hrs.

Through the preparation method, the 2 ethanesulfonic acid salt of N-hydroxy-4-{5-[4-(5-isopropyl-2-methyl-1,3-thiazol-4-yl)phenoxy]pentoxy}benzamidine may be produced in a high yield of 86% or more.

In a further aspect, the present invention relates to a pharmaceutical composition for preventing and treating osteoporosis, bone fractures or allergic inflammatory diseases, comprising the 2 ethanesulfonic acid salt of N-hydroxy-4-{5-[4-(5-isopropyl-2-methyl-1,3-thiazol-4-yl)phenoxy]pentoxy}benzamidine.

As used herein, the term "osteoporosis", which is also called 'osteopenia', indicates a condition that features the excess loss of inorganic and organic matrix of bone with no structural abnormality in the remaining bone, leading to the bone to be full of tiny holes like a sponge and thus compressible and fragile. The excellent clinical efficacy of the N-hydroxy-4-{5-[4-(5-isopropyl-2-methyl-1,3-thiazol-4-yl)phenoxy]pentoxy}benzamidine compound in the prevention and treatment of osteoporosis is described in detail in Korean Patent No. 10-454767 and International No. WO/03007947.

As used herein, the term "bone fractures", which describes a state in which the continuity of bone tissue is disrupted completely or incompletely, includes various physical injuries of the bone, which are classified based on anatomic location (epiphyseal, metaphyseal, diaphyseal and intra-articular, or proximal, middle and distal, etc.), severity of fractures (complete, incomplete, etc.), direction of fractures (transverse, oblique, spiral, longitudinal, etc.), the presence of open wounds (open, closed), the number of fracture fragments (simple or linear, comminuted, segmental, etc.), stabil- <Reaction Scheme 1>

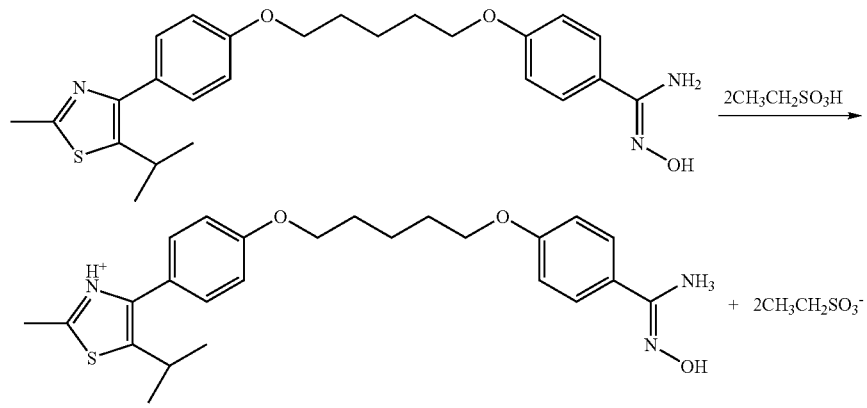

The ethanesulfonic acid used in the preparation method according to the present invention, which is a salt that has been approved for use in drugs by the US FDA, is a colorless stable liquid that is not hygroscopic and not corrosive. Also, since the ethanesulfonic acid is not toxic, it provides a safe environment during production, and since it is easy to handle, it can be readily mass-produced.

The inert solvent used in the preparation method according to the present invention includes ethyl acetate, methanol, ethanol, isopropanol, acetone, acetonitrile, hexane, and isopropyl ether. Of these, ethanol is preferred.

ity of fractures (stable, unstable), and the degree of displacement of fracture fragments. In rats, the N-hydroxy-4-{5-[4-(5-isopropyl-2-methyl-1,3-thiazol-4-yl)phenoxy]pentoxy}benzamidine compound significantly reduced callus volume, significantly enhanced bone mineral content and mechanical strength of callus, significantly reduced the content of connective and soft tissues in the callus tissue, and significantly increased bone tissue density, as compared to a control not treated with the benzamidine compound (Korean Patent NO. 10-639041).

As used herein, the term "allergic inflammatory diseases", refers to non-specific inflammatory diseases caused by a variety of allergens, and includes allergic rhinitis, asthma, allergic conjunctivitis, allergic dermatitis, atopic dermatitis, contact dermatitis, urticaria, anaphylaxis, insect allergy, food allergy, and drug allergy.

The preventive and therapeutic efficacy of the N-hydroxy-4-{5-[4-(5-isopropyl-2-methyl-1,3-thiazol-4-yl)phenoxy]pentoxy}benzamidine compound on allergic inflammatory diseases was confirmed in a mouse model of asthma which was induced by chronic exposure to ovalbumin. The benzamidine compound was administered for a period of 18 days, starting on the day of immunization with ovalbumin. 15 days after immunization, experimental animals were challenged with ovalbumin, and sacrificed three days later to investigate lung weight, changes in the cellular profile of peripheral blood samples and bronchoalvelar lavage fluid, and histopathological changes in lung tissue. The oral administration of the benzamidine compound suppressed the increase in lung weight, as compared to a control administered only with sterile distilled water. The total number of leukocytes and the number of eosinophils significantly increased in asthmatic mice, as compared to normal mice, but significantly decreased in asthmatic mice administered with the benzamidine compound in a dose-dependent manner, as compared to the control group. Also, the number of eosinophils in bronchoalveolar lavage fluid significantly increased in asthmatic mice, as compared to normal mice, but significantly decreased in asthmatic mice administered with the benzamidine compound in a dose-dependent manner, as compared to the control group. The asthmatic mice administered with the benzamidine compound exhibited significantly increased alveolar area, as compared to the control group (Korean Patent NO. 10-682199).

In addition to the aforementioned component, the composition of the present invention may further include one or more pharmaceutically acceptable carriers. The pharmaceutically acceptable carriers may include ordinary excipients, disintegrants, humectants, fillers, thickeners, binders, lubricants, glidants, antioxidants, buffering agents, surfactants, dispersing agents, and their combinations of two or more.

The composition of the present invention may be administered orally or parenterally. For oral administration, the composition may be formulated into solid forms, for example, tablets, capsules, pills or powders; or into liquid forms, for example, suspensions, syrups or solutions. For parenteral administration (e.g., intravenous, sub-cutaneous, intraperitoneal, intranasal, etc.), the composition may be formulated into injections, ointments, patches, or the like. These formulations may be suitably made depending on the type of diseases or ingredients according to a proper method known in the art or a method described in the literature: Remington's Pharmaceutical Science (recent version), Mack Publishing Company, Easton Pa.

Preferably, oral formulations may be prepared using one or more carbonates selected from the group consisting of alkali metal carbonate, alkali metal bicarbonate and alkaline earth metal carbonate, and/or one or more disintegrants selected from the group consisting of sodium carboxymethyl starch, calcium carmellose and sodium croscarmellose. This formulation increases remarkably enhances the release rate and bioavailability by suppressing the gelation of the 2 ethanesulfonic acid salt upon contact with water in the early stage of release. The aforementioned carbonate and/or disintegrant regionally forms a neutral pH or weak alkaline environment in the diffusion layer contacting with water during release of the 2 ethanesulfonic acid salt, or rapidly disperses the composition, thereby effectively suppressing the gelation caused by hydration in the early stage of release.

The carbonate used in the oral formulations is selected from the group consisting of alkali metal carbonate such as sodium carbonate, and potassium carbonate; alkali metal bicarbonate such as sodium bicarbonate, and potassium bicarbonate; and alkaline earth metal carbonate such as calcium carbonate, and magnesium carbonate. Sodium bi-carbonate or calcium carbonate is preferred. The carbonate may be contained in an amount of about 0.4 to 6 parts by weight, preferably 0.5 to 2 parts by weight, based on one part by weight of the 2 ethanesulfonic acid salt. In the case where the carbonate is used in an amount of less than 0.4 parts by weight, the release rate of the compound is not enhanced. Carbonate of greater than 6 parts by weight generates gas in the gastrointestinal tract and thus causes abdominal swelling.

The disintegrant used in the oral formulations is one or more selected from the group consisting of sodium carboxymethyl starch, sodium carmellose, calcium carmellose, and sodium croscarmellose. Sodium carboxymethyl starch or sodium croscarmellose is preferred. The disintegrants rapidly absorb water and largely swell in the early stage of release to disperse particles of 2 ethansulfonic acid salt of Formula 1, thereby effectively suppressing gelation beginning on the surface of formulations, resulting in increased release rates of the compound. The content of the disintegrant ranges from 0.5 to 5 parts by weight, based on one part by weight of the 2 ethanesulfonic acid salt of the above formula. In the case where the disintegrant is used in an amount of less than 0.5 parts by weight, the drug is not evenly dispersed, leading to a decrease in the suppressive effect of the carrier against gelation in the early stage of release, and eventually resulting in no improvement in the release rate of the drug. The disintegrant of greater than 5 parts by weight does not exhibit an enhancing effect on the release rates of the drug any more, and enlarges the volume of the formulations, thereby causing inconvenience upon ingestion of the drug and resulting in decreased patient compliance.

The oral formulation may be prepared by mixing the 2 ethanesulfonic acid salt with both the disintegrant and carbonate. The combinational use of the disintegrant and carbonate improves the release properties of the drug relative to single use. In the case of the combinational use of the disintegrant and carbonate, the oral formulation of the present invention preferably contains the disintegrant in an amount of 0.5 to 5 parts by weight and the carbonate in an amount of 0.1 to 6 parts by weight, based on one part by weight of the 2 ethanesulfonic acid salt. In the case where the disintegrant and carbonate are used in amounts of less than 0.5 and 0.1 parts by weight, respectively, they do not exhibit a suitable inhibitory effect on gelation. In the case where the amounts of disintegrant and carbonate exceed 5 and 6 parts by weight, respectively, satisfactory patient compliance is not achieved.

In addition, the oral formulation may further include an excipient. In order to increase the release rate of the drug by effectively inhibiting gelation and thus rapidly dispersing the drug, the excipient is preferably an inorganic excipient such as calcium biphosphate, calcium phosphate, heavy magnesium oxide, precipitated calcium carbonate, and magnesium carbonate. More preferred is calcium biphosphate, calcium phosphate, or heavy magnesium oxide. In contrast, organic excipients, such as avicel, mannitol, corn starch and lactose, have no enhancing effect on the release rate of the drug.

In addition, the oral formulation may further a pharmaceutically-acceptable ordinary additive. Examples of the additive include binders, glidants, surfactants, colorants, and taste/smell masking agents. Pharmaceutically-acceptable ordinary binders and glidants are available. The binders are exemplified by maltose, Arabia gum and hydroxypropyl-cellulose. The glidants are exemplified by carnauba wax, light anhydrous silicic acid, synthetic aluminum silicate, stearic acid, magnesium stearate, and talc.

In addition to the aforementioned components, the oral formulation may include a pharmaceutically-acceptable ordinary excipient or adjuvant, and may be formulated into a solid formulation for oral administration, such as tablets, capsules, granules, and fine granules, through an ordinary pharmaceutical method. That is, according to the present invention, the composition may be formulated as granules, and may be supplemented with a glidant and other pharmaceutically acceptable additives, and directly filled into hard capsules in a powder or granule form. Otherwise, the composition may be supplemented with pharmaceutical additives for tabletting and compressed to produce tablets according to a known method.

The dosage of the composition of the present invention may vary according to the patient's weight, age, gender, health state and diet, administration duration, administration routes, excretion rates, severity of the illness, and the like. The 2 ethanesulfonic acid salt of N-Hydroxy-4-{5-[4-(5-isopropyl-2-methyl-1,3-thiazol-4-yl)phenoxy]pentoxy}benzamidine of Formula 1 may be administered, for example, in a daily dosage of 1 to 1,000 mg/kg, preferably 10 to 500 mg/kg. The daily dosage may be divided into one to several doses.

The present composition may be used singly or in combination with surgical operation, hormone therapy, drug therapy and biological response regulators in order to prevent and treat osteoporosis, bone fractures and allergic inflammatory diseases.

A better understanding of the present invention may be obtained through the following examples which are set forth to illustrate, but are not to be construed as the limit of the present invention.

MODE FOR THE INVENTION

Example 1

Preparation of N-hydroxy-4-{5-[4-(5-isopropyl-2-methyl-1,3-thiazol-4-yl)phenoxy]pentoxy}benzamidine 2 ethansulfonic acid salt 3 g (6.614 mmol) of N-hydroxy-4-{5-[4-(5-isopropyl-2-methyl-1,3-thiazol-4-yl)phenoxy]pentoxy}benzamidine was dissolved in 30 ml of ethanol, and was mixed with 1.14 ml (2.2 equivalents) of ethanesulfonic acid with agitation at room temperature for 1 hr. The solution was then mixed with 30 ml of acetone and 60 ml of hexane with agitation for 1 hr. The produced solid was recovered by filtration, washed with acetone, and dried under vacuum. As a result, 4.17 g (yield: 86%) of N-Hydroxy-4-{5-[4-(5-isopropyl-2-methyl-1,3-thiazol-4-yl)phenoxy]pentoxy}benzamidine 2 ethansulfonic acid salt was obtained as a white solid.

The obtained N-Hydroxy-4-{5-[4-(5-isopropyl-2-methyl-1,3-thiazol-4-yl)phenoxy]pentoxy}benzamidine 2 ethansulfonic acid salt was analyzed for the content of ethanesulfonic acid and melting point, and the results are as follows.

Content of ethanesulfonic acid (Theoretical value: 32.7%, Measured value: 33.0%),
Melting point: 141° C.

Comparative Example 1

Preparation of N-hydroxy-4-{5-[4-(5-isopropyl-2-methyl-1,3-thiazol-4-yl)phenoxy]pentoxy}benzamidine N-hydroxy-4-{5-[4-(5-isopropyl-2-methyl-1,3-thiazol-4-yl)phenoxy]pentoxy}benzamidine was prepared according to a method described in the literature: Lee, Sung-Eun, Synthesis and Biological Activity of Natural Products and Designed New Hybrid Compounds for the treatment of LTB4 Related Disease, the doctoral thesis, the Graduate School, Busan National University, 1999 August).

Comparative Example 2

Preparation of N-hydroxy-4-{5-[4-(5-isopropyl-2-methyl-1,3-thiazol-4-yl)phenoxy]pentoxy}benzamidine 2 methansulfonic acid salt An N-hydroxy-4-{5-[4-(5-isopropyl-2-methyl-1,3-thiazol-4-yl)phenoxy]pentoxy}benzamidine 2 methansulfonic acid salt was prepared according to the method described in Korean Patent Publication No. 10-2006-57511.

Experimental Example 1

Evaluation of Solubility

The N-hydroxy-4-{5-[4-(5-isopropyl-2-methyl-1,3-thiazol-4-yl)phenoxy]pentoxy}benzamidine 2 ethansulfonic acid salt prepared in Example 1, the N-hydroxy-4-{5-[4-(5-isopropyl-2-methyl-1,3-thiazol-4-yl)phenoxy]pentoxy}benzamidine prepared in Comparative Example 1, and the N-hydroxy-4-{5-[4-(5-isopropyl-2-methyl-1,3-thiazol-4-yl)phenoxy]pentoxy}benzamidine 2 methansulfonic acid salt prepared in Comparative Example 2 were examined for solubility (μg/ml) in various solvents at room temperature.

The results are given in Table 1, below.

TABLE 1

| | Used salt | | |
|---|---|---|---|
| Solvent | free base | 2 Methansulfonic acid salt | 2 Ethansulfonic acid salt |
| Distilled water | 3.48 | 3,535 | 4,421 |

As shown in Table 1, the 2 ethanesulfonic acid salt of N-hydroxy-4-{5-[4-(5-isopropyl-2-methyl-1,3-thiazol-4-yl)phenoxy]pentoxy}benzamidine exhibited 1.25-fold higher solubility than the 2 methansulfonic acid salt thereof.

Experimental Example 2

Evaluation of Release Rate

The N-hydroxy-4-{5-[4-(5-isopropyl-2-methyl-1,3-thiazol-4-yl)phenoxy]pentoxy}benzamidine 2 ethansulfonic acid salt prepared in Example 1, the N-hydroxy-4-{5-[4-(5-isopropyl-2-methyl-1,3-thiazol-4-yl)phenoxy]pentoxy}benzamidine prepared in Comparative Example 1, and the N-hydroxy-4-{5-[4-(5-isopropyl-2-methyl-1,3-thiazol-4-yl)phenoxy]pentoxy}benzamidine 2 methansulfonic acid salt prepared in Comparative Example 2 were examined for release rate (%) in a buffer solution (pH 1.2) at a paddle rotation speed of 50 rpm.

The results are given in Table 2, below.

TABLE 2

| | | Used salt | |
|---|---|---|---|
| Time (min) | Free base | 2 Methansulfonic acid salt | 2 Ethansulfonic acid salt |
| 5 | 1.2 | 5.3 | 14.8 |
| 10 | 3.5 | 13.9 | 20.5 |
| 15 | 7.9 | 20.1 | 24.2 |
| 30 | 21.3 | 34.3 | 31.3 |

As shown in Table 2, the 2 ethansulfonic acid salt of N-hydroxy-4-{5-[4-(5-isopropyl-2-methyl-1,3-thiazol-4-yl)phenoxy]pentoxy}benzamidine exhibited the release rate about 2.8-fold higher after 5 min, about 1.4-fold higher after 10 min, and about 1.2-fold higher after 15 min, as compared to the 2 methanesulfonic acid salt thereof.

Experimental Example 3

Evaluation of Stability

The N-hydroxy-4-{5-[4-(5-isopropyl-2-methyl-1,3-thiazol-4-yl)phenoxy]pentoxy}benzamidine 2 ethansulfonic acid salt prepared in Example 1 was placed into a transparent glass vial, and stored at a cap-opened state under accelerated conditions (60° C.±2/75% RH±5) for a period of two weeks. Thereafter, the sample was analyzed by HPLC (Waters Module 1). The analysis was performed using a column packed with an octadecyl-silylated silica gel (Shiseido CAPCELL PAK C18, UG 120, Particle size 5 μm) under conditions: UV detection: 256 nm, injection volume: 10 μl, mobile-phase flow rate: 1.5 mL/min. The amount of the compound was calculated as an area percentage.

The results are given in Table 3, below.

TABLE 3

| | Content (%) |
|---|---|
| Early stage | 100.00 |
| After 1 week | 99.88 |
| After 2 weeks | 99.86 |

As shown in Table 3, the accelerated test at 60° C. resulted in no change in content of the N-hydroxy-4-{5-[4-(5-isopropyl-2-methyl-1,3-thiazol-4-yl)phenoxy]pentoxy}benzamidine 2 ethansulfonic acid salt in distilled water. Also, the N-hydroxy-4-{5-[4-(5-isopropyl-2-methyl-1,3-thiazol-4-yl)phenoxy]pentoxy}benzamidine 2 ethansulfonic acid salt was found to have high chemical stability at high temperature.

Experimental Example 4

Pharmacokinetic Evaluation (Bioavailability)

The N-hydroxy-4-{5-[4-(5-isopropyl-2-methyl-1,3-thiazol-4-yl)phenoxy]pentoxy}benzamidine 2 ethansulfonic acid salt prepared in Example 1, and the N-hydroxy-4-{5-[4-(5-isopropyl-2-methyl-1,3-thiazol-4-yl)phenoxy]pentoxy}benzamidine 2 methansulfonic acid salt prepared in Comparative Example 2 were individually administered to SD rats in a dosage of 50 mg/kg. At given time points (0, 0.5, 1, 1.5, 2, 3, 5 and 8 hrs), rats were mildly anesthetized with diethyl ether, and blood samples were collected from the orbital venous plexus and stored at −20° C. until concentration analysis. The plasma samples were mixed with an equal volume of an internal standard substance solution (prepared by dissolving betamethasone in acetonitrile to give a final concentration of 30 μg/ml) with agitation for 1 min, and was centrifuged at 12,000 rpm for 10 min. Active components of the plasma samples were analyzed by HPLC (Model: Waters Module 1). From the obtained data, pharmacokinetic parameters [maximum blood concentration (Cmax) and area under the blood concentration-time curve (AUC)] were calculated by noncompartment analysis using the WinNonlin program (Version 1.0, Scientific Consulting Inc., USA).

The results are given in Table 4, below.

TABLE 4

| | Used salt | |
|---|---|---|
| | 2 Methanesulfonic acid salt | 2 Ethanesulfonic acid salt |
| Dosage | 50 mg/kg | 50 mg/kg |
| Rat no. | 4 | 4 |
| Cmax (μg/ml) | 1.792 ± 0.912 | 2.360 ± 0.183 |
| Tmax (hr) | 3.00 ± 1.63 | 2.13 ± 0.63 |
| AUC (μg/ml) | 8.967 ± 3.091 | 10.848 ± 0.833 |

As shown in Table 4, in distilled water, the N-hydroxy-4-{5-[4-(5-isopropyl-2-methyl-1,3-thiazol-4-yl)phenoxy]pentoxy}benzamidine 2 ethansulfonic acid salt exhibited high bioavailability of 1.3-fold higher Cmax (maximum blood concentration), 1.4-fold faster Tmax (time to reach maximum plasma concentration), and about 1.2-fold higher AUC (area under the blood concentration-time curve), as compared to the 2 methanesulfonic acid salt of the benzamidine compound.

INDUSTRIAL APPLICABILITY

The 2 ethanesulfonic acid salt of N-Hydroxy-4-{5-[4-(5-isopropyl-2-methyl-1,3-thiazol-4-yl)phenoxy]pentoxy}benzamidine according to the present invention has excellent solubility, stability, and bioavailability, as well as a high initial release rate, as compared to the 2 methansulfonic acid salt thereof. In particular, since the 2 ethanesulfonic acid salt of N-Hydroxy-4-{5-[4-(5-isopropyl-2-methyl-1,3-thiazol-4-yl)phenoxy]pentoxy}benzamidine exhibited higher Cmax (maximum blood concentration) and AUC (area under the blood concentration-time curve), and faster Tmax (time to reach maximum plasma concentration), its blood concentration rapidly reaches effective level, resulting in more rapid drug action. Thus, having enhanced bioavailability, the 2 ethanesulfonic acid salt of N-Hydroxy-4-{5-[4-(5-isopropyl-2-methyl-1,3-thiazol-4-yl)phenoxy]pentoxy}benzamidine is useful for preventing or treating osteoporosis, bone fractures and allergic inflammatory diseases even at low concentrations.

The invention claimed is:

1. An N-hydroxy-4-{5-[4-(5-isopropyl-2-methyl-1,3-thiazol-4-yl)phenoxy]pentoxy} benzamidine 2 ethansuifonic acid salt, represented by the following formula 1

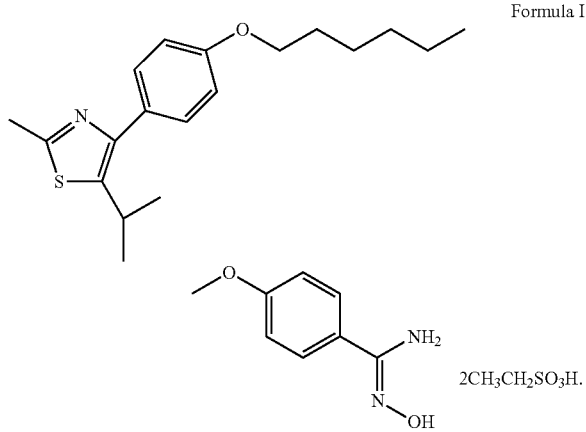

Formula I

2CH₃CH₂SO₃H.

2. A process for preparing the N-hydroxy-4-{5-[4-(5-isopropyl-2-methyl-1,3-thiazol-4-yl)phenoxy]pentoxy} benzamidine 2 ethansulfonic acid salt of claim 1, comprising the steps of reacting N-hydroxy-4-{5-[4-(5-isopropyl-2-methyl-1,3-thiazol-4-yl)phenoxy]pentoxy} benzamidine 2 ethansulfonic acid in an inert solvent.

3. The process according to claim 2, wherein the inert solvent is one or more selected from the group consisting of ethyl acetate, methanol, ethanol, isopropanol, acetone, acetonitrile, hexane, and isopropyl ether.

4. A pharmaceutical composition comprising the N-hydroxy-4-{5-[4-(5-isopropyl-2-methyl-1,3-thiazol-4- yl)phenoxy]pentoxy}-benzamidine 2 ethansulfonic acid salt of claim 1 and a pharmaceutically acceptable carrier.

5. An oral formulation comprising the N-hydroxy-4-{5-[4-(5-isopropyl-2-methyl-1,3-thiazol-4-yl)phenoxy]pentoxy}-benzarnidine 2 ethansulfonic acid salt of claim 1, along with (a) one or more carbonates selected from the group consisting of alkali metal carbonate, alkali metal bicarbonate and alkaline earth metal carbonate; (b) one or more disintegrants selected from the group consisting of sodium carboxymethyl starch, sodium carmellose, calcium carmellose and sodium croscarmellose; or a combination of (a) and (b).

6. The oral formulation according to claim 5, wherein the carbonate is sodium bicarbonate or calcium carbonate, and the disintegrant is sodium carboxymethyl starch or sodium croscarmellose.

7. The oral formulation according to claim 5 or 6, further comprising an inorganic excipient.

8. The oral formulation according to claim 7, wherein the inorganic excipient is calcium biphosphate, calcium phosphate, heavy magnesium oxide, precipitated calcium carbonate, magnesium carbonate, or a mixture thereof.

9. A method for treating osteoporosis in a patient in need thereof which method comprises administering to said patient a compound represented by formula 1 of claim 1.

10. A method for treating osteoporosis in a patient in need thereof which method comprises administering to said patient a pharmaceutical composition of claim 4.

* * * * *